US009101728B1

(12) United States Patent
Al-Wazzan et al.

(10) Patent No.: US 9,101,728 B1
(45) Date of Patent: Aug. 11, 2015

(54) ENDOTRACHEAL TUBE

(71) Applicants: Lila H. A. J. Al-Wazzan, Hawally (KW); Ali Wazzan, Hawally (KW)

(72) Inventors: Lila H. A. J. Al-Wazzan, Hawally (KW); Ali Wazzan, Hawally (KW)

( * ) Notice: Subject to any disclaimer, the term of this patent is extended or adjusted under 35 U.S.C. 154(b) by 0 days.

(21) Appl. No.: 14/316,755

(22) Filed: Jun. 26, 2014

(51) Int. Cl.
*A61M 16/04* (2006.01)
*A61B 1/06* (2006.01)
*A61M 25/09* (2006.01)
*A61M 16/00* (2006.01)
*A61B 1/267* (2006.01)

(52) U.S. Cl.
CPC .............. *A61M 16/0488* (2013.01); *A61B 1/06* (2013.01); *A61B 1/267* (2013.01); *A61M 16/0003* (2014.02); *A61M 16/0051* (2013.01); *A61M 16/0069* (2014.02); *A61M 16/044* (2013.01); *A61M 25/09* (2013.01); *A61M 2016/003* (2013.01)

(58) Field of Classification Search
CPC . A61M 16/00; A61M 16/0051; A61M 16/04; A61M 16/0434; A61M 16/0486; A61M 2016/0015; A61M 2016/0027; A61M 2016/003; A61M 2016/0033; A61M 2016/0036; A61M 2016/0039; A61M 2016/0042; A61M 2205/587; A61M 25/01; A61M 25/0102; A61M 25/0105; A61B 1/06; A61B 1/0607; A61B 1/0615; A61B 1/0623; A61B 1/063; A61B 1/267
USPC .............. 128/207.14–207.17, 202.27, 204.23, 128/205.23, 200.26, 204.18; 606/108
See application file for complete search history.

(56) References Cited

U.S. PATENT DOCUMENTS

| | | | | |
|---|---|---|---|---|
| 4,150,676 A | * | 4/1979 | Jackson | 128/207.18 |
| 5,095,900 A | * | 3/1992 | Fertig et al. | 128/207.14 |
| 5,277,175 A | | 1/1994 | Riggs et al. | |
| 6,694,978 B1 | * | 2/2004 | Bennarsten | 128/204.21 |
| 8,505,533 B2 | | 8/2013 | Raphael et al. | |
| 2005/0039754 A1 | * | 2/2005 | Simon | 128/207.14 |
| 2009/0198111 A1 | | 8/2009 | Nearman et al. | |
| 2009/0322867 A1 | | 12/2009 | Carrey et al. | |
| 2011/0109458 A1 | | 5/2011 | Shipman | |
| 2012/0138058 A1 | | 6/2012 | Fu et al. | |

OTHER PUBLICATIONS

"Tracheal tube," http://en.wikipedia.org/wiki/Tracheal_tube. (4 pages) (Last Accessed on May 30, 2014).

* cited by examiner

*Primary Examiner* — Justine Yu
*Assistant Examiner* — Michael Tsai
(74) *Attorney, Agent, or Firm* — Richard C Litman

(57) ABSTRACT

An endotracheal tube includes an elongated, flexible shaft having a proximal end and a distal end, the distal end including a tip having a first section and a second section, the shaft having a lumen extending therethrough, at least one light strip positioned in association with and extending along the elongated, flexible shaft to illuminate at least a portion of the shaft including the distal end of the shaft to illuminate at least a portion of a pathway into the trachea, and a connector positioned in communicating relation with the proximal end of the shaft adapted to receive a fluid medium to flow through the lumen, the connector being in communication with the at least one light strip. The endotracheal tube can also be adapted to include a balloon in communication with the distal end of the shaft within the trachea to occlude a portion of the trachea.

10 Claims, 4 Drawing Sheets

ENDOTRACHEAL TUBE

BACKGROUND OF THE INVENTION

1. Field of the Invention

The present invention generally relates to medical devices, and more particularly to an endotracheal tube having at least one light strip extending along the endotracheal tube adapted to illuminate a pathway through a patient's mouth or nose into the patient's trachea, an inflatable balloon adapted to occlude the patient's airway, and a connector having an alarm mechanism including a speaker and/or a light to alert a medical professional if the connector becomes disconnected.

2. Description of the Related Art

Intubation is an invasive procedure in which a medical practitioner uses an endotracheal tube to maintain an open airway for a patient. It can also be a method through which to administer certain medication, such as anesthesia. The procedure is typically done by having a medical practitioner insert an endotracheal tube into a patient's mouth (also known as a tracheal intubation) or nose (also known as a nasal intubation) and feeds the distal end of the endotracheal tube into the trachea of the patient to provide a fluid medium, such as air, oxygen, an air or a gas mixture or certain medications, into the lungs of the patient. This is typically done when a person cannot manage their own airway, either because of injury and/or trauma suffered by a person or because of general anesthesia received in preparation for a medical procedure. The goal of an intubation is to insert the endotracheal tube into the trachea of the patient and then maintain it within the trachea without causing damage to the patient's trachea until the procedure is complete and the endotracheal tube is removed.

Whether such goal of intubation is achieved can depend on a variety of factors, such as the skill of the medical practitioner and the instruments being used to see the opening of the trachea, for example. Despite the relatively high number of intubations that are performed on a daily basis, complications can arise as a result of improper or difficult intubations. Factors that can lead to complications include, for example, vocal cords not being visible despite the patient's mouth being opened, variations in normal anatomy, pathologic conditions which do not allow the medical practitioner to see the tracheal opening, and instrument malfunctioning.

Also, for example, should the light on a laryngoscope fail during an intubation the medical practitioner could thread the endoscope into the patient's esophagus instead of the trachea. Such a mistake could result in serious injuries and even death of the patient. Moreover, if a connector of the endotracheal tube were to become disconnected from a ventilator or the shaft inside the patient's body without anyone noticing, the patient could die as a result of lack of oxygen, a condition known as hypoxia.

Thus, an endotracheal tube addressing the aforementioned problems is desired.

SUMMARY OF THE INVENTION

Embodiments of an endotracheal tube includes an elongated, flexible shaft, having a proximal end, a distal end including a tip having a first section and a second section, and a lumen extending therethrough, the lumen including an interior portion and an exterior portion. It can be appreciated that the first section of the tip can extend beyond the second section of the tip to form a beveled tip. The endotracheal tube also includes at least one light strip having a proximal end and a distal end and positioned in association with and extending along the elongated, flexible shaft, such as from the proximal end of the elongated, flexible shaft to the distal end of the elongated, flexible shaft, and a connector positioned in communicating relation with the proximal end of the elongated, flexible shaft adapted to receive a fluid medium, such as air, oxygen, an air or a gas mixture or medication(s), to flow through the lumen into the patient. The connector also is in communication with the proximal end of the at least one light strip, wherein the at least one light strip is adapted to illuminate at least a portion of the pathway from a patient's mouth or nose into the trachea.

Embodiments of an endotracheal tube can also include a power source coupled to the connector and positioned in communication with the proximal end of the at least one light strip, and can include at least one guide wire positioned in communication with the shaft, such as extending along the length of the elongated, flexible shaft, from the proximal end to the distal end of the elongated, flexible shaft adapted to control the configuration of the elongated, flexible shaft.

Embodiments of an endotracheal tube can also include a sensor positioned in communication with the connector adapted to detect an interruption in the flow of the fluid medium to the patient and activate an alert mechanism, such as a light, such as an indicator light, for example, that emits a visual alert, such as a blinking light, for example, and/or a speaker, such as a micro-speaker, for example, that emits an audible alert, such as a beeping sound, for example, to alert a medical practitioner of an interruption of the flow of the fluid medium to the patient. The connector can also include an alarm controller to selectively deactivate the alert mechanism once the interruption of the flow of the fluid medium to the patient has been corrected and a light strip controller to selectively activate and deactivate the at least one light strip.

Further, embodiments of an endotracheal tube can include a balloon positioned in communication with the distal end of the elongated, flexible shaft adapted to position and align the endotracheal tube within a patient's trachea to occlude the patient's airway and to enable the flow of the fluid medium into the patient's lungs. It is to be noted that the endotracheal tube can be adapted to include an inflation port in communication with a delivery line positioned in communication with the elongated, flexible shaft adapted to deliver an inflation medium to the balloon to inflate the balloon.

These and other features of the present invention will become readily apparent upon further review of the following specification and drawings.

BRIEF DESCRIPTION OF THE DRAWINGS

Unless otherwise indicated, similar reference characters denote corresponding features consistently throughout the attached drawings.

DETAILED DESCRIPTION OF THE PREFERRED EMBODIMENTS

Figure 1:
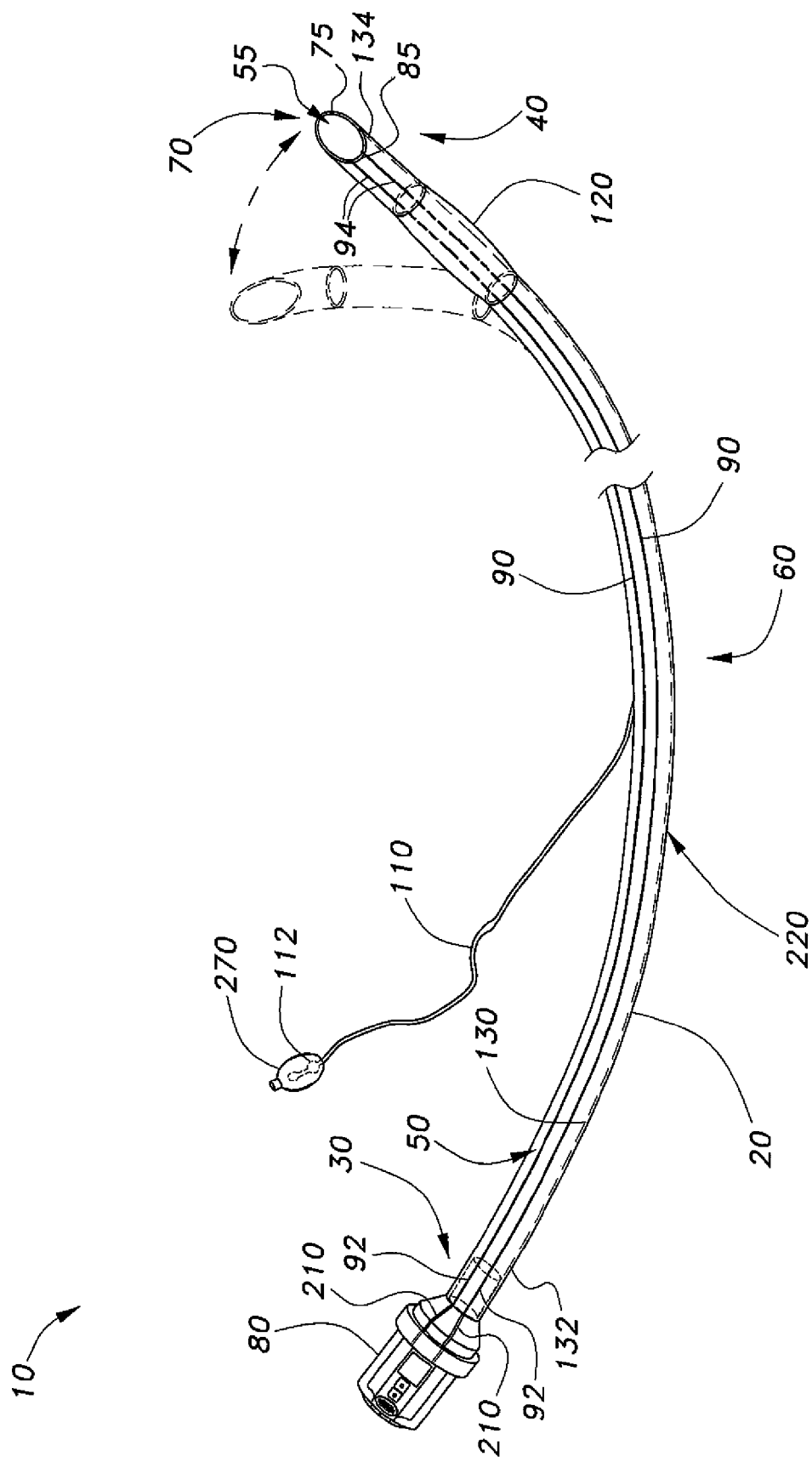
FIG. 1 is an environmental, perspective view of an endotracheal tube according to the present invention.

Referring to FIGS. 1 through 4, an embodiment of an endotracheal tube, generally identified as 10, is illustrated.

The endotracheal tube 10 generally includes an elongated, flexible shaft 20, having a proximal end 30, a distal end 40 including a tip 70 having a first section 75 and a second section 85, and a lumen 55 extending through the elongated, flexible shaft 20, the lumen 55 including an interior portion 50 and an exterior portion 60. It is to be appreciated that the first section 75 of the tip 70 can be adapted to extend beyond the second section 85 of the tip 70 to form a beveled tip 70. The beveled tip 70 can be formed in a suitable configuration of the first section 75 and the second section 85 to provide an angle suitable to allow the elongated, flexible tip 70 of the shaft 20 to enter the trachea 250 through the patient's mouth 240, as can depend on the particular use or application, for example.

The endotracheal tube 10 also includes at least one light strip 90, such as a flexible light emitting diode (LED) light strip, for example, having a proximal end 92 and a distal end 94. The at least one light strip 90 is positioned in association with the elongated, flexible shaft 20, such as the within, extending through or along the interior portion 50 or the exterior portion of the lumen 55 of the elongated, flexible shaft 20, such as from the proximal end 30 of the elongated, flexible shaft 20 to the distal end 40 of the elongated, flexible shaft 20, for example, and is adapted to illuminate at least a portion of the elongated, flexible shaft 20 including the distal end 40 of the elongated, flexible shaft 20 to illuminate at least a portion of a pathway into the trachea 250. It is to be noted that the at least one light strip 90 can include LED lights extending from the proximal end 92 of the at least one light strip 90 to the distal end 94 of the at least one light strip 90, or along portions thereof, for example, and should not be construed in a limiting sense.

The endotracheal tube 10 further includes a connector 80 positioned in a selectively detachable communicating relation with the proximal end 30 of the elongated, flexible shaft 20 adapted to receive a fluid medium, such as air, oxygen, an air or a gas mixture or medication(s), to flow through the lumen 55 into the patient. The connector 80 also is in selectively detachable communication with the proximal end 92 of the at least one light strip 90, such as through at least one wire 210, wherein the at least one light strip 90 is adapted to illuminate at least a portion of the pathway from a patient's mouth 240 or nose 280 into the trachea 250. It is to be noted that the light emanating from the at least one light strip 90 can be a yellow light, for example, or other suitable color, as can depend on the use or application, and should not be construed in a limiting sense.

It is contemplated that the endotracheal tube 10 can be adapted to include a power source 100 coupled to or in conjunction with the connector 80 and positioned in selectively detachable communicating relation to the proximal end 92 of at least one light strip 90, such as through the at least one wire 210. Also the endotracheal tube 10 can include at least one guide wire 130 having a proximal end 132 and a distal end 134 and positioned in association with the elongated, flexible shaft 20, such as in association with the interior portion 50 or the exterior portion 60 of the lumen 55, such as extending along the interior portion 50 of the lumen 55, extending along the exterior portion 60 of the lumen 55, or extending in a portion of the elongated, flexible shaft 20 formed between the interior portion 50 and the exterior portion 60 of the lumen 55, from the proximal end 30 of the elongated, flexible shaft 20 to the distal end 40 of the elongated, flexible shaft 20.

The at least one guide wire 130 adapted to control the configuration of the elongated, flexible shaft 20, such as to be curved as it is inserted through the patient's mouth 240 or nose 280 into the trachea 250, for example. Also the endotracheal tube 10 can include a balloon 120 in communication with the distal end 40 of the elongated, flexible shaft 20, the balloon 120 being adapted to position and align the distal end 40 of the elongated, flexible shaft 20 within the trachea 250 and to occlude a portion of the trachea 250 and can assist in enabling the flow of the fluid medium, such as air, oxygen, an air or a gas mixture or medication(s), through the lumen 55 and out through the distal end 40 of the elongated, flexible shaft 20.

The endotracheal tube 10 can also be adapted to include an inflation port 112 in communication with a delivery line 110 positioned in communication with the elongated, flexible shaft 20 adapted to deliver an inflation medium, such as a saline solution, air or a gaseous mixture, for example, to the balloon 120 to inflate the balloon 120. The inflation port 112 is in communication with an inflation medium connector 270 to connect the inflation port 112 and the delivery line 110 to a source of an inflation medium. It is to be appreciated that the distal end 40 of the elongated, flexible shaft 20 can be adapted to include a camera, such as a micro-camera, so as to visualize the position of the endotracheal tube 10 within the patient's trachea 250, an example of such positioning of the endotracheal tube 10 being shown in FIG. 4.

Also, it is desirable that the connector 80 can be removably securable to a ventilator, such as a suitable ventilator machine or a suitable ventilator device, for example. The connector 80 can be adapted to include a sensor 215 positioned in communication with the connector 80 adapted to detect an interruption in the flow of the fluid medium, such as air, oxygen, an air or a gas mixture or medication(s), for example, and to selectively activate an alert mechanism, such as a light 140, such as an indicator light, for example, that emits a visual alert, such as a blinking light, for example, and/or a speaker 150, such as a micro-speaker, for example, that emits an audible alert, such as a beeping sound, for example, to alert a medical practitioner to an interruption in the flow of the fluid medium to the patient, such as the disconnection of the connector 80 from the proximal end 30 of the elongated, flexible shaft 20, for example. The sensor 215 can also be adapted to selectively activate the alert mechanism, such as the light 140 and/or the speaker 150, if the connector 80 and the ventilator device become disconnected or the connector 80 and the elongated, flexible shaft 20 become disconnected, or the flow of the fluid medium becomes otherwise disrupted, for example.

The elongated, flexible shaft 20 can include a wall 220 of substantially uniform thickness allowing the lumen 55 having the interior portion 50 and the exterior portion 60 to be adapted to receive the at least one light strip 90, as well as other medical implements. Also, the at least one guide wire 130 can be adapted to be positioned with or integrated within the wall 220 of the elongated, flexible shaft 20, for example. The elongated, flexible shaft 20 can be formed from any suitable, medical grade material. It is desirable, however, that the elongated, flexible shaft 20 be formed from a flexible tubular member having a braided construction.

The elongated, flexible shaft 20 can be adapted for intubation through the mouth 240 into the trachea 250, as well as through the nasal cavity of the nose 280 into the trachea 250. Also, embodiments of the tracheal tube 10 including the elongated, flexible shaft 20 can also be adapted to be used in conjunction with a tracheotomy by being inserted into an opening created in the neck into the trachea 250 for delivery of the fluid medium into a patient, for example.

The braided construction of the elongated, flexible shaft 20, as can also provide kink resistance, can enhance the ability to push the elongated, flexible shaft 20 when threading the endotracheal tube 10 through the mouth 240 or the nose 280 and through the trachea 250 into or proximate to the patient's lungs 260. It is to be noted that the elongated, flexible shaft 20 can be adapted to include a distinctive indicia, such as color-coding, markings, and/or etchings along the entire length of, or along one or more portions of, the elongated, flexible shaft 20 to indicate an orientation and a depth of penetration into the trachea 250 of the patient.

It is to be noted that the length, configuration and dimensions of the elongated, flexible shaft 20 can vary, such as depending on whether the patient is a neonate, a child, an adolescent, an adult, male, or female, as can also depend on the particular use or application, for example. It is desirable, however, that the length of the elongated, flexible shaft 20 be in the range of about 7.5 cm to 26 cm, for example, and should not be construed in a limiting sense.

The balloon 120, associated with the endotracheal tube 10, is in communication with the distal end 40 of the elongated, flexible shaft 20 and can be formed from various suitable, medical grade, and puncture-resistant material, such as polyethylene terephthalate (PET), nylon, polyurethane, and other elastomers, as can depend on the particular use or application, and should not be construed in a limiting sense. The balloon 120 can also be adapted to expand to a specific size or be in a suitable configuration, such as a size and/or configuration required to occlude the patient's trachea 250 and to assist in preventing or substantially preventing the fluid medium, such as air, oxygen, an air or a gas mixture or medication(s), from escaping or flowing back through the trachea 250 after delivery of the fluid medium into the patient, such as into the patient's lungs 260, for example.

The balloon 120 can be produced in a wide range of diameters, lengths, and shapes, such as conical, spherical, or tapered, for example, and should not be construed in a limiting sense. It is desirable, however, that the balloon 120 have a suitable length and shape sufficient to occlude the patient's trachea 250 and to hold or substantially hold the elongated, flexible shaft 20 in position within the trachea 250 to enable the flow of the fluid medium into the lungs 260 of the patient. The balloon 120 can also be coated with a suitable lubricating medium for lubrication or for abrasion resistance during use of the endotracheal tube 10 with a patient.

Figure 2:
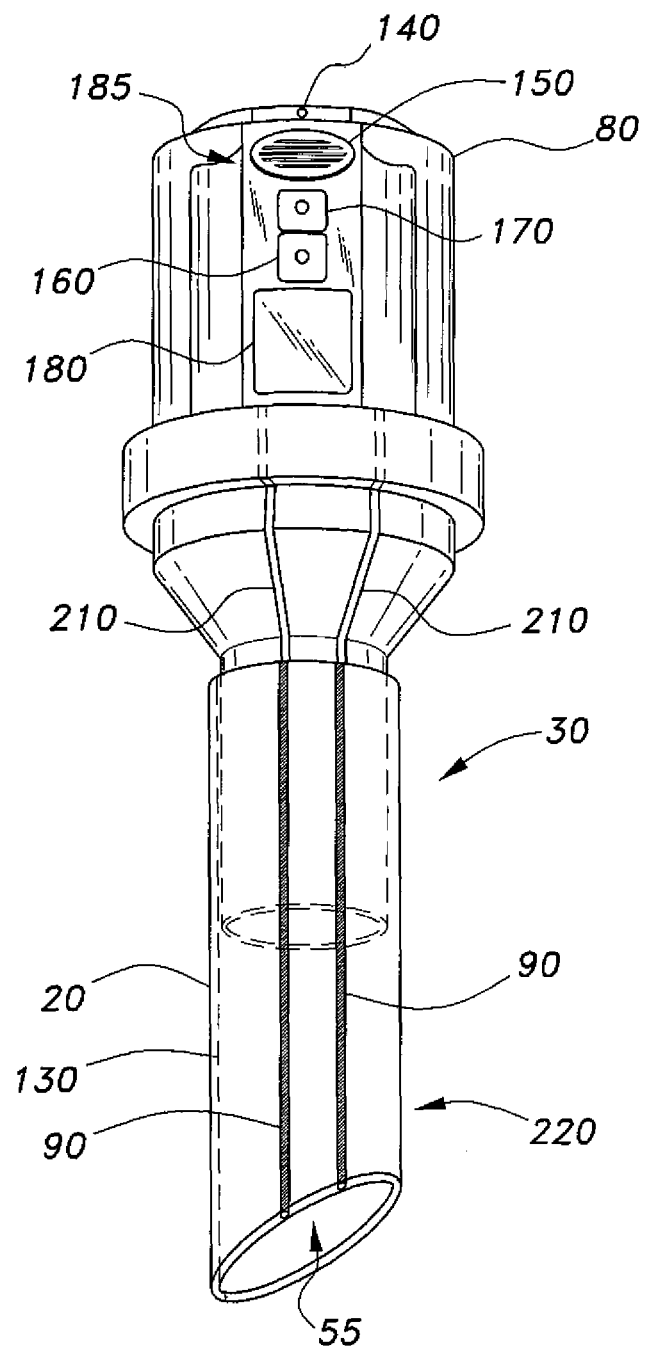
FIG. 2 is a front view of a connector of the endotracheal tube according to the present invention.
Figure 3:
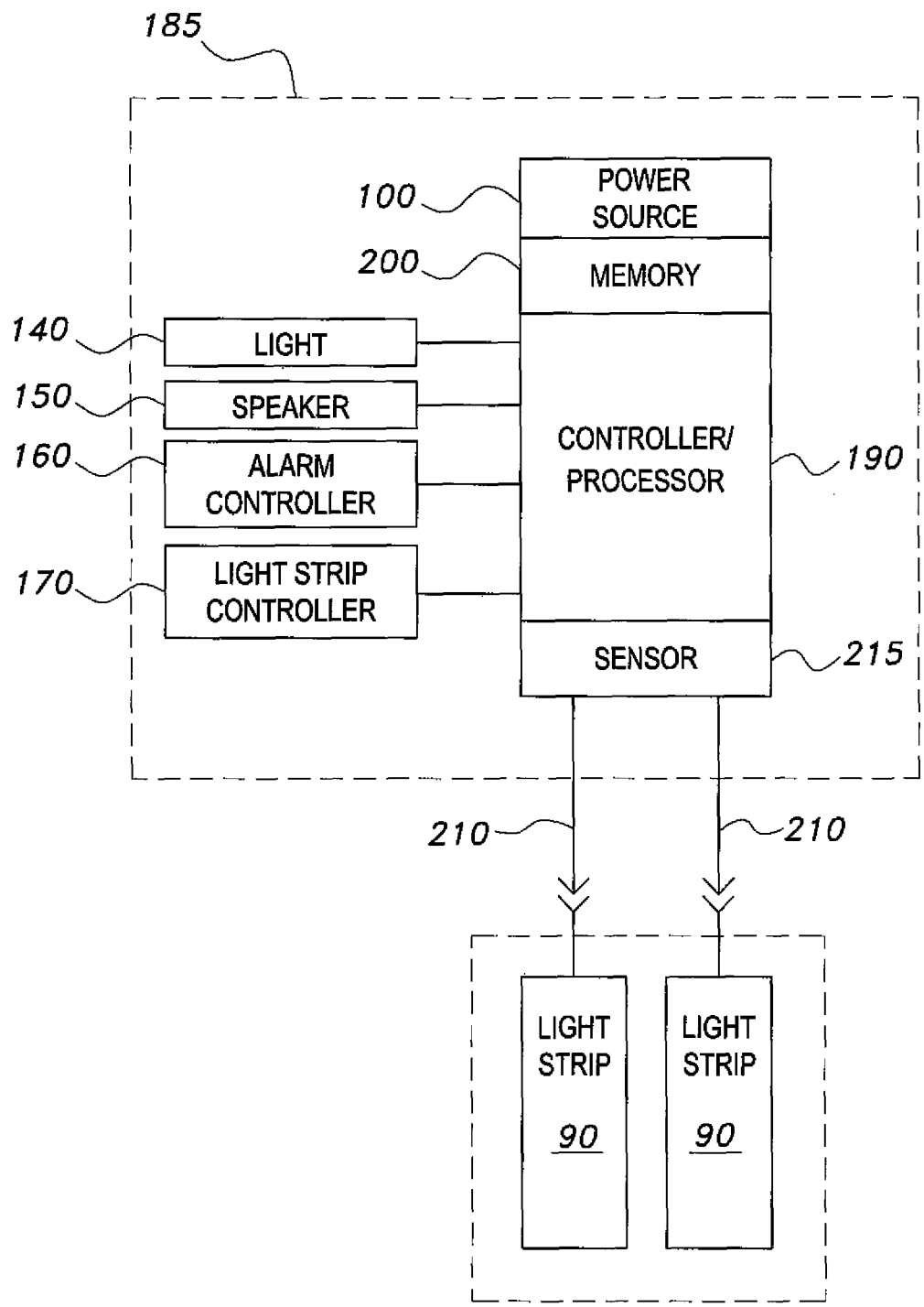
FIG. 3 is a schematic diagram of a control system for use in combination with embodiments of the endotracheal tube of FIG. 1 according to the present invention.

Referring to FIGS. 1, 2 and 3, the connector 80 can also include or be associated with a control system 185 as can include an alarm controller 160, such as a switch or a button, for example, to selectively deactivate the alert mechanism included in or associated with the control system 185, such as the light 140 and/or the speaker 150 in communication with the connector 80. The control system 185 also can include a light strip controller 170, such as a switch or a button or other suitable controller, for example, to selectively activate and deactivate the at least one light strip 90, and can include at least one battery port 180 to house the power source 100 to power the components of or associated with the endotracheal tube 10 using electrical power, such as the described components of the control system 185 and the at least one light strip 90, for example. It is to be noted that the connector 80 included or associated with the control system 185 is not inserted into the patient's mouth 240 or the patient's nose 280, as illustrated and indicated from FIG. 4, for example.

Referring to FIG. 3, the control system 185 can include a controller/processor 190 and an associated memory 200 as can store instructions implemented by the controller/processor 190 for operation of the components of the control system 185, as well as store data and information related to use and operation of the endotracheal tube 10, for example. It should be understood that various components of the control system 185, such as the controller/processor 190 and other components of the control system 185, can be implemented as, for example, a microcontroller, an application specific integrated circuit (ASIC), or a programmable logic controller (PLC), for example, and should not be construed in a limiting sense. The controller/processor 190 can be any suitable type of computer processor, such as a microprocessor or an ASIC, and the calculations, determinations, data transmission or data reception, sending or receiving of control signals or commands related to use and operation of the endotracheal tube 10 are processed or controlled by the controller/processor 190.

The controller/processor 190 is in communication with the light 140, the speaker 150, the alarm controller 160 to selectively deactivate the light 140 and/or speaker 150, the light strip controller 170 to selectively activate and deactivate the at least one light strip 90, the memory 200 to receive instructions therefrom or to store data and information therein. The controller/processor 190 is also in communication with a sensor 215 included in the control system 185, such as a flow sensor and/or a power interruption sensor, adapted to selectively activate the alert mechanism if there is an interruption in the flow of the fluid medium to the patient or a disconnection of the connector 80 from the elongated, flexible shaft 20 or from a ventilator device, for example. Also, the components of the control system 180 can be in communication with one another by any suitable type of data bus, as is known in the art.

The memory 200 can be any suitable type of computer readable and programmable memory. Examples of computer readable media include a magnetic recording apparatus, non-transitory computer readable storage memory, an optical disk, a magneto-optical disk, and/or a semiconductor memory (for example, RAM, ROM, etc.). Examples of magnetic recording apparatus that may be used in addition to memory, or in place of memory, include a hard disk device (HDD), a flexible disk (FD), and a magnetic tape (MT). Examples of the optical disk include a DVD (Digital Versatile Disc), a DVD-RAM, a CD-ROM (Compact Disc-Read Only Memory), and a CD-R (Recordable)/RW.

Figure 4:
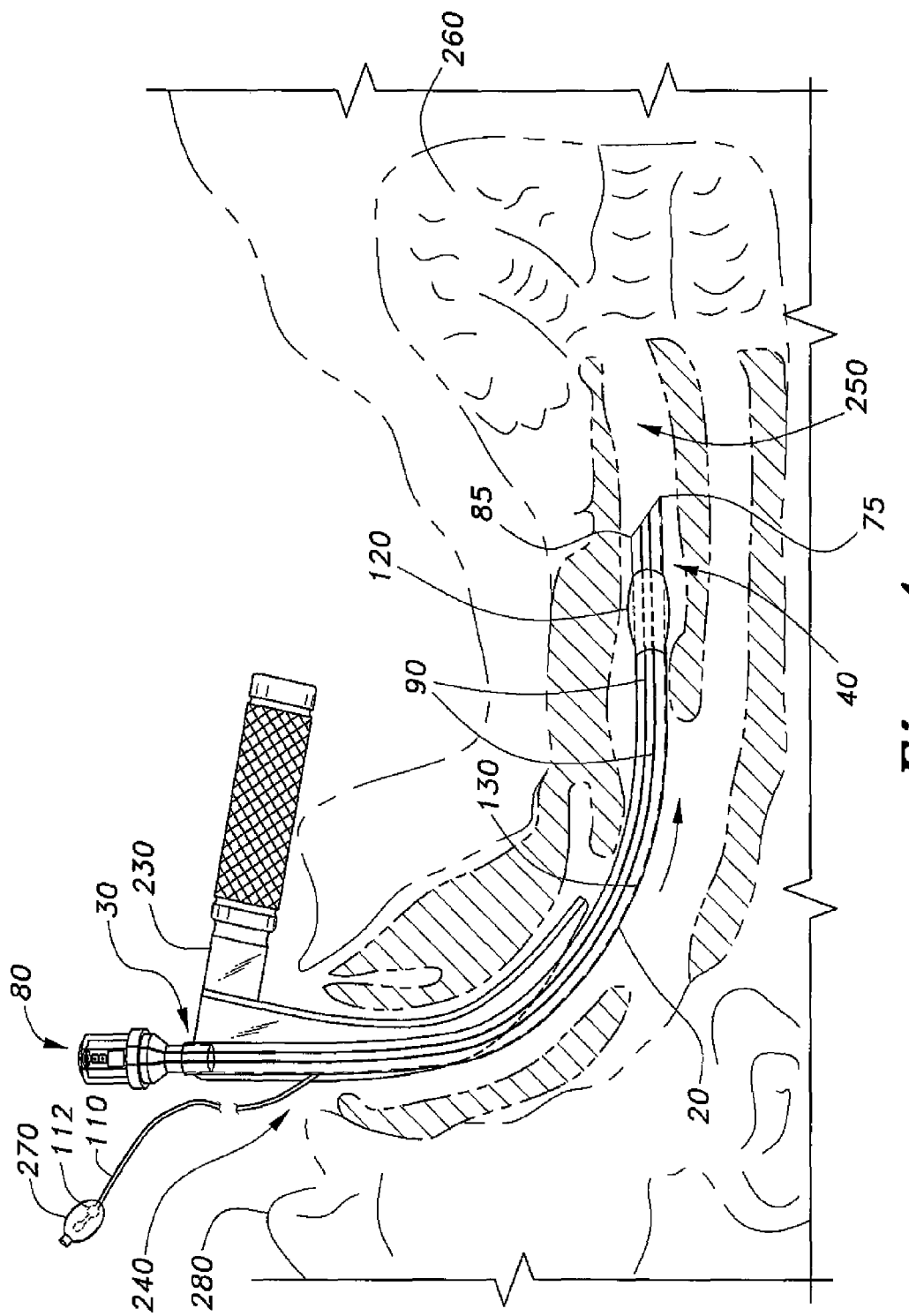
FIG. 4 is a side view of an embodiment of the endotracheal tube of FIG. 1 and also illustrating an embodiment of the endotracheal tube being used in a method of intubation according to the present invention.

Referring to FIGS. 2, 3 and 4, the power source 100 can include a suitable power supply, such as a direct current (DC) power supply derived from a battery, such as a 3 volt DC battery, for example. The electric charge delivered to the at least one light strip 90 from the power source 100 to cause the illumination of the at least one light strip 90 is delivered through the at least one wire 210 in communication with the corresponding at least one light strip 90.

The illumination of the at least one light strip 90 causes the endotracheal tube 10 to illuminate to enhance and assist the medical practitioner in visualizing at least a portion of the pathway through the patient's mouth 240 or nose 280 and the trachea 250, to assist in threading the elongated, flexible shaft 20 through the trachea 250 and into or in proximity to the lungs 260 of the patient. It is to be noted that the power source 100 can be used to power the control system 185 and components thereof, such as the controller/processor 190, the alarm controller 160, the light strip controller 170, the alert mechanism, such as the light 140 and/or the speaker 150, the sensor 215, and a micro-camera associated with the endotracheal tube 10, for example.

By way of operation and use of the endotracheal tube 10, once the patient starts to have trouble maintaining or to open an airway, either because of injury, trauma or anesthesia in preparation for a medical procedure, a medical practitioner inserts a laryngoscope 230 into the mouth 240 to open the patient's airway. After the medical practitioner opens the patient's airway using the laryngoscope 230, the medical practitioner begins to insert the distal end 40 of the elongated, flexible shaft 20 into the patient's mouth 240. It is to be noted that the elongated, flexible shaft 20 can also be inserted into the trachea 250 by inserting the elongated, flexible shaft 20 though the patient's nose 280.

Prior to inserting the elongated, flexible shaft 20 into the patient's mouth 240 or nose 280 or as the medical practitioner is inserting the elongated, flexible shaft 20 into the patient's mouth 240 or nose 280, the medical practitioner activates the at least one light strip 90 by activating on the light strip controller 170 so as to assist the medical practitioner in visualizing at least a portion of the pathway through the mouth 240 or nose 280 into and through the trachea 250 for passing the endotracheal tube 10.

Once the elongated, flexible shaft 20 has been inserted into the patient's trachea 250 so that the tip 70 or the distal end 40 of the elongated, flexible shaft 20 is located at an appropriate or sufficient depth within the trachea 250, the medical practitioner can use the inflation port 112 in communication with the delivery line 110 positioned in communication with the elongated, flexible shaft 20 to deliver an inflation medium, such as air, a gaseous mixture or a saline solution, for example, into the balloon 120 to inflate the balloon 120 to occlude the patient's airway and to ensure that the fluid medium, such as air, oxygen, an air or a gas mixture or medication(s), reaches the patient's lungs 260 and does not escape or flow back through the patient's trachea 250, as well as to hold or substantially hold the elongated, flexible shaft 20 in place while the medical practitioner completes the medical procedure.

After the endotracheal tube 10 has been inserted into the trachea 250 and the balloon 120 has been inflated, the medical practitioner can connect the connector 80 of the endotracheal tube 10 to the ventilator, such as a suitable ventilating or fluid medium providing device or apparatus, to allow the fluid medium to flow through the lumen 55 and into the patient's lungs 260. Once the medical procedure has been completed, the medical practitioner can open the inflation port 112 and deflate the balloon 120 so as to be able to remove the elongated, flexible shaft 20 from the patient's trachea 250.

If the connector 80 positioned in communication with the proximal end 30 of the elongated, flexible shaft 20 detaches from the elongated, flexible shaft 20 resulting in an interruption in the flow of the fluid medium to the patient, the sensor 215 can send a signal to the controller/processor 190 in the control system 185 so as to activate the alert mechanism, such as the light 140 to emit a visual signal, such as a flashing light, for example, and/or the speaker 150 to emit an audible alert, such as a beeping sound, for example. Once the connector 80 has been reconnected to the proximal end 30 of the elongated, flexible shaft 20 or to the ventilator device, and the interruption in the flow of the fluid medium to the patient has been corrected, the medical practitioner can use the alarm controller 160 to selectively deactivate the visual alert and the audible alert.

It is to be understood that the present invention is not limited to the embodiments described above, but encompasses any and all embodiments within the scope of the following claims.

We claim:

1. An endotracheal tube, comprising:
    an elongated, flexible shaft having a proximal end and a distal end, the distal end including a tip having a first section and a second section, the elongated, flexible shaft having a lumen extending therethrough;
    at least one light strip positioned in association with and extending along the elongated, flexible shaft to illuminate at least a portion of the elongated, flexible shaft including the distal end of the elongated, flexible shaft to illuminate at least a portion of a pathway into the trachea; and
    a connector, the connector comprising a one-piece housing and being positioned in direct communicating relation with the proximal end of the elongated, flexible shaft adapted to receive a fluid medium to flow through the lumen and out through the distal end of the elongated, flexible shaft, the connector being in direct communication with the at least one light strip, wherein the connector further includes: i) at least one wire detachably communicating with a corresponding at least one light strip; ii) a light strip controller adapted to activate and deactivate the at least one light strip; iii) a sensor adapted to detect an interruption in the flow of the fluid medium into the lumen to activate an alert mechanism to indicate the interruption in the flow of the fluid medium; and iv) an alarm controller adapted to deactivate the alert mechanism.

2. The endotracheal tube according to claim 1, further comprising:
    a balloon in communication with the distal end of the elongated, flexible shaft, the balloon being adapted to position and align the distal end of the elongated, flexible shaft within the trachea and to occlude a portion of the trachea to substantially prevent the fluid medium that has flowed through the lumen and out through the distal end of the elongated, flexible shaft to flow back through the trachea.

3. The endotracheal tube according to claim 2, further comprising:
    an inflation port in communication with a delivery line adapted to deliver an inflation medium to the balloon to inflate the balloon.

4. The endotracheal tube according to claim 1, further comprising:
    at least one guide wire positioned in association with the elongated, flexible shaft and extending along the elongated, flexible shaft to control a configuration of the elongated, flexible shaft.

5. The endotracheal tube according to claim 1, wherein the first section of the tip extends beyond the second section of the tip to form a beveled tip.

6. A method of intubating a patient, comprising the steps of:
    providing an endotracheal tube comprising an elongated, flexible shaft and a connector in selectively detachable communication at a proximal end of the elongated, flexible shaft;
    providing at least one light strip positioned in association with and extending along the elongated, flexible shaft to illuminate at least a portion of the elongated, flexible shaft including the distal end of the elongated, flexible shaft to illuminate at least a portion of a pathway into the trachea;
    providing a connector, the connector comprising a one-piece housing and being positioned in direct communicating relation with the proximal end of the elongated, flexible shaft adapted to receive a fluid medium to flow through the lumen and out through the distal end of the elongated, flexible shaft, the connector being in direct communication with the at least one light strip, wherein the connector further includes: i) at least one wire detachably communicating with a corresponding at least one light strip; ii) a light strip controller adapted to activate and deactivate the at least one light strip; iii) a sensor adapted to detect an interruption in the flow of the fluid medium into the lumen to activate an alert mechanism to indicate the interruption in the flow of the fluid medium; and iv) an alarm controller adapted to deactivate the alert mechanism;

attaching the connector of the endotracheal tube to a ventilation device to deliver a fluid medium through a lumen extending through the elongated, flexible shaft;

activating the at least one light strip positioned in association with the elongated, flexible shaft extending along the elongated, flexible shaft to illuminate at least a portion of the elongated, flexible shaft including a distal end of the elongated, flexible shaft to illuminate at least a portion of a pathway into the trachea;

inserting the elongated, flexible shaft of the endotracheal tube into the pathway into the trachea; and inflating a balloon in communication with the distal end of the elongated, flexible shaft to position and align the distal end of the elongated, flexible shaft within the trachea to flow the fluid medium through the lumen and out through the distal end of the elongated, flexible shaft and to occlude a portion of the trachea to substantially prevent the fluid medium that has flowed through the lumen and out through the distal end of the elongated, flexible shaft to flow back through the trachea.

7. The method of intubating a patient according to claim 6, further comprising the step of:
selectively opening the patient's airway by inserting a laryngoscope into the patient's mouth.

8. The method of intubating a patient according to claim 6, further comprising the step of:
controlling by at least one guide wire positioned in association with the elongated, flexible shaft and extending along the elongated, flexible shaft a configuration of the elongated, flexible shaft flexible when positioned in the pathway into the trachea.

9. The method of intubating a patient according to claim 6, further comprising the steps of:
detecting an interruption in the flow of the fluid medium by a sensor; and
activating an alert mechanism associated with the connector to indicate the detected interruption in the flow of the fluid medium.

10. The method of intubating a patient according to claim 9, further comprising the step of:
deactivating the alert mechanism by an alarm controller associated with the connector.

* * * * *